United States Patent
Wiand

(10) Patent No.: US 10,064,702 B2
(45) Date of Patent: Sep. 4, 2018

(54) VACUUM BRAZED DIAMOND DENTAL BURR MADE USING SYNTHETIC DIAMOND

(71) Applicant: Inland Diamond Products Company, Madison Heights, MI (US)

(72) Inventor: Ronald C. Wiand, Troy, MI (US)

(73) Assignee: Inland Diamond Products Company, Madison Heights, MI (US)

( * ) Notice: Subject to any disclaimer, the term of this patent is extended or adjusted under 35 U.S.C. 154(b) by 12 days.

(21) Appl. No.: 14/689,545

(22) Filed: Apr. 17, 2015

(65) Prior Publication Data

US 2015/0297318 A1    Oct. 22, 2015

Related U.S. Application Data

(60) Provisional application No. 61/980,897, filed on Apr. 17, 2014.

(51) Int. Cl.
*A61C 3/02* (2006.01)
(52) U.S. Cl.
CPC ...................................... *A61C 3/02* (2013.01)

(58) Field of Classification Search
CPC ........................................................ A61C 3/02
See application file for complete search history.

(56) References Cited

U.S. PATENT DOCUMENTS

| | | | | |
|---|---|---|---|---|
| 4,681,541 A | * | 7/1987 | Snaper | A61C 3/02 408/144 |
| 4,776,862 A | | 10/1988 | Wiand | |
| 4,931,069 A | * | 6/1990 | Wiand | B24B 13/01 451/541 |
| 4,968,326 A | | 11/1990 | Wiand | |
| 5,492,771 A | * | 2/1996 | Lowder | B23K 35/327 428/546 |
| 2007/0111161 A1 | * | 5/2007 | Strauss | A61C 3/06 433/166 |
| 2009/0301788 A1 | * | 12/2009 | Stevens | B22F 7/062 175/374 |

* cited by examiner

*Primary Examiner* — Rex R Holmes
(74) *Attorney, Agent, or Firm* — Warn Partners, P.C.

(57) ABSTRACT

A dental burr and process of manufacture having a synthetic diamond grit abrasive portion. The dental burr includes a dental burr tool substrate including a shaft portion and a working portion. The working portion contains on its outer surface a synthetic diamond abrasive grit cutting surface. The synthetic diamond is brazedly attached to the surface.

16 Claims, 3 Drawing Sheets

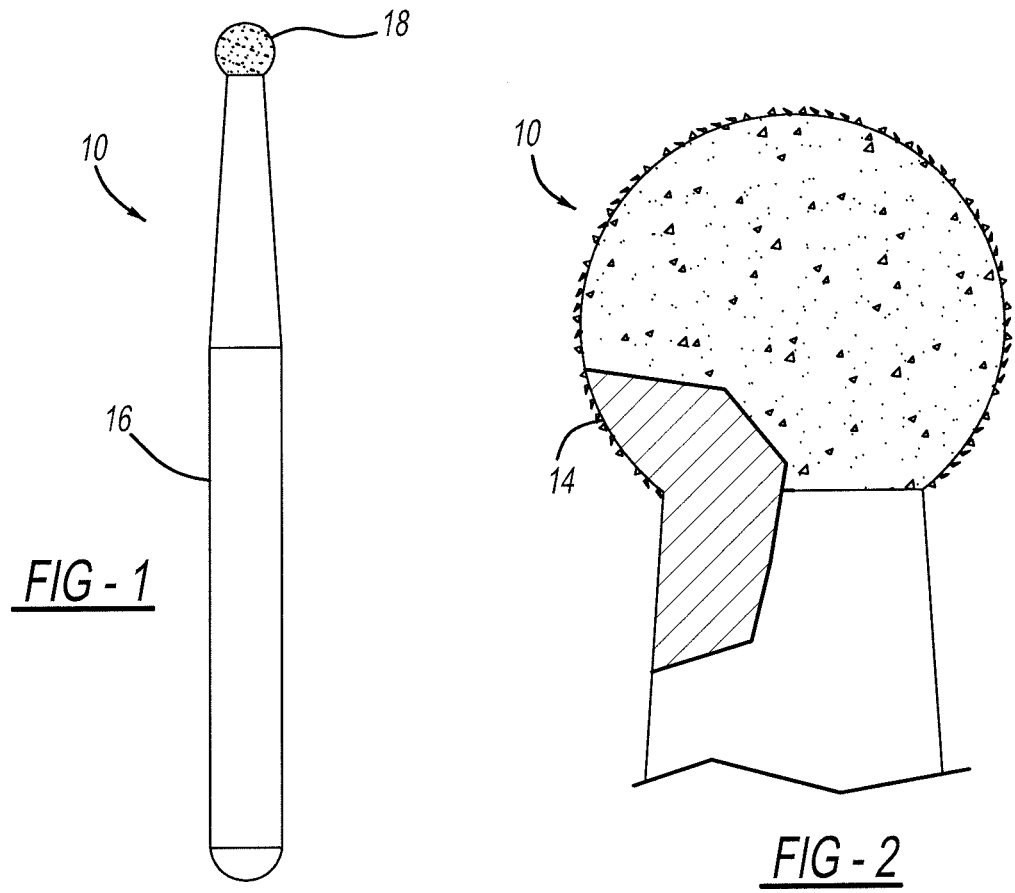
FIG - 1
FIG - 2
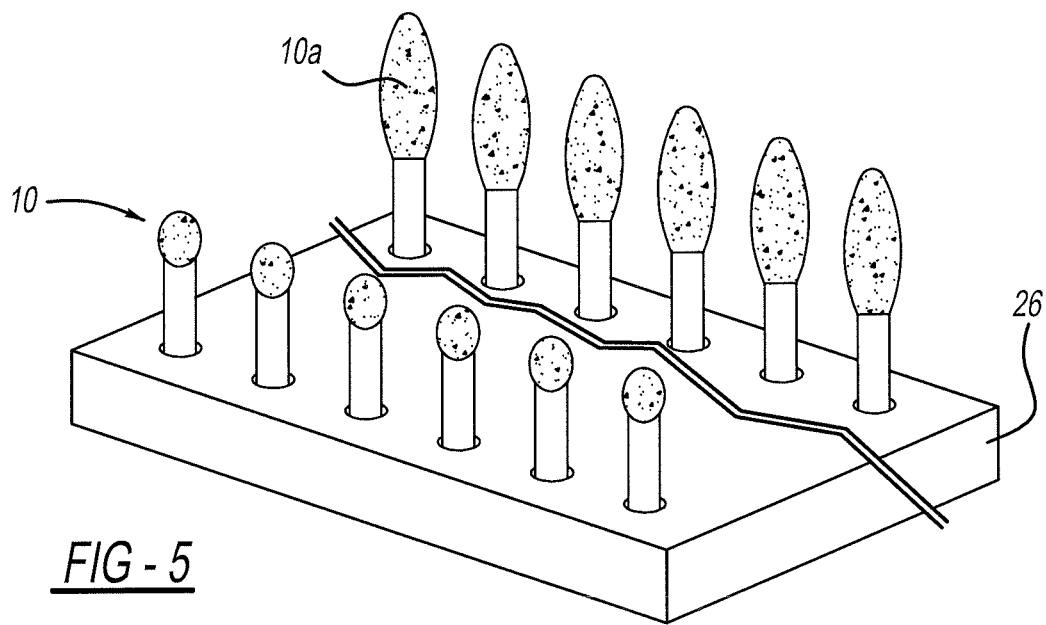
FIG - 5

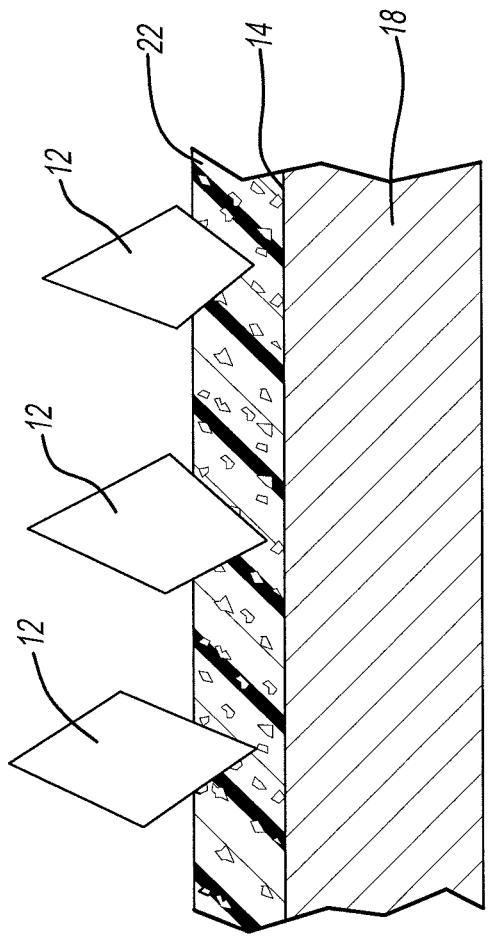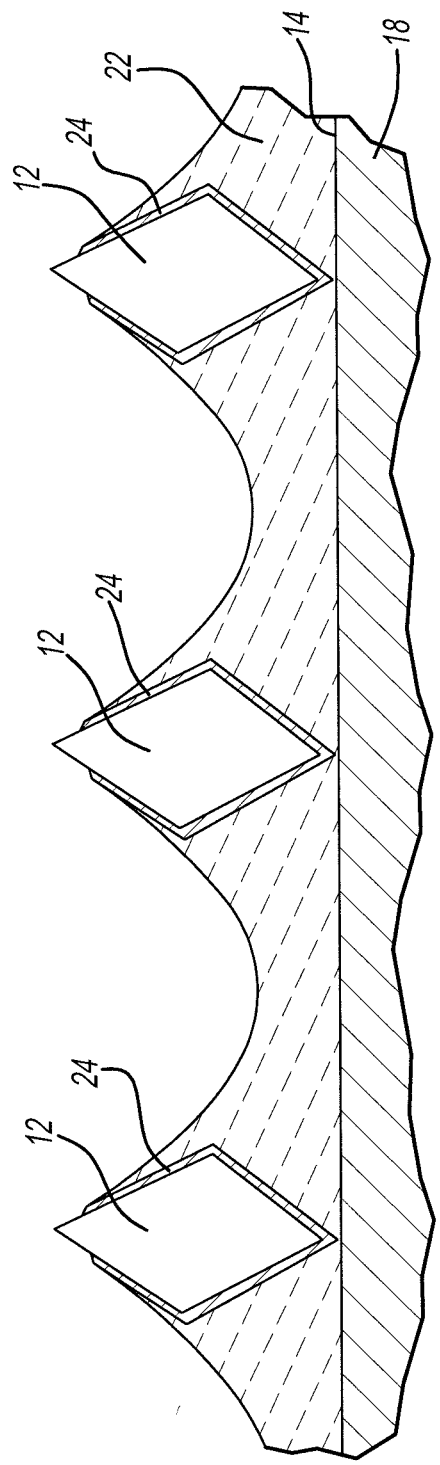

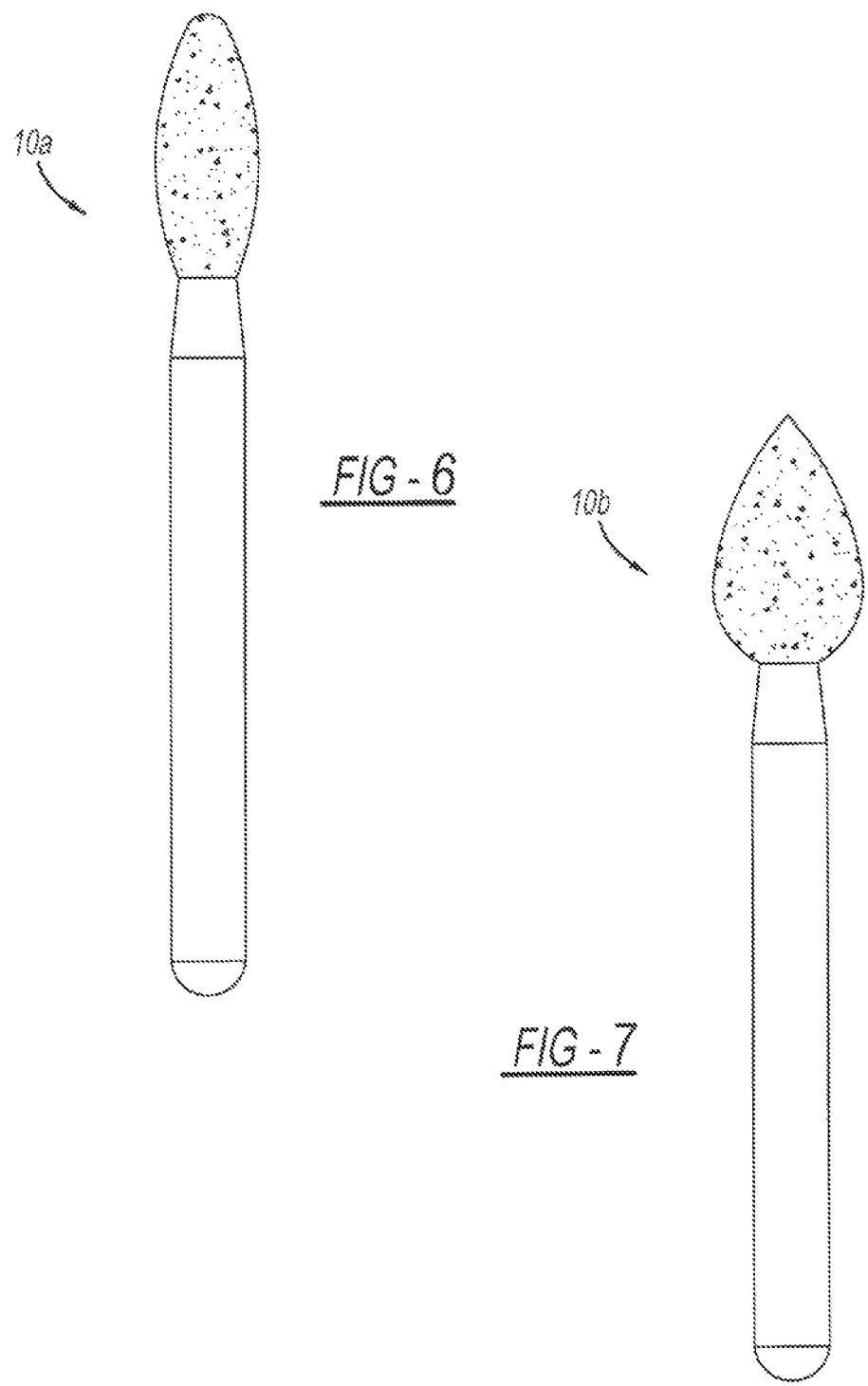

US 10,064,702 B2

VACUUM BRAZED DIAMOND DENTAL BURR MADE USING SYNTHETIC DIAMOND

FIELD OF THE INVENTION

The present invention relates to a dental burr tool.

BACKGROUND OF THE INVENTION

Diamond dental burrs are made using a nickel electroplating process that co-deposits diamond and nickel onto a small dental burr core or mandrel and are made using natural diamond not synthetic diamond. The only known supplier of brazed diamond dental burrs also uses natural diamond as stated in their product specifications.

Electroplated diamond tools are not made using synthetic diamond, they are made using natural diamond, the FDA has only approved natural diamond for use in dental burrs.

There are several new materials entering the dental market for making crowns, caps, bridges and dentures. These materials are extremely difficult to grind as they are extremely hard materials, much harder than the conventional dental materials. These new materials like zirconia and Maicor™ will take over the market and will be very difficult to grind using dental burrs made using natural diamond. Natural diamond is very friable and the electroplated bonds are relatively weak. The modern dental materials are so hard that electroplated burrs with natural diamond will not be adequate for grinding and working of these materials. It is believe that it would take more than one electroplated diamond dental burr to grind a standard tooth containing the material.

Therefore, there is a need in the art to provide a robust dental burr that will withstand the rigors of grinding modern dental materials.

SUMMARY OF THE INVENTION

A dental burr having a synthetic diamond grit abrasive head portion. The dental burr includes a dental burr tool substrate including a shaft portion and a working portion. The working portion contains on its outer surface a synthetic diamond abrasive grit cutting surface. The synthetic diamond is brazedly attached to the surface.

A process for manufacture of a dental burr is also provided. The process includes providing a dental burr tool including a shaft portion and a cutting head portion; coating the cutting head portion with a mixture of a braze and synthetic diamond material; and heating the dental burr at a temperature for brazing of the diamond to the cutting head.

Tougher synthetic diamond, which has not been processed for use in electroplated diamond tools can grind the new dental materials used in crowns, caps, bridges and dentures with at least twice the grinding efficiency as natural diamond and if it is bonded to a dental burr blank by a vacuum brazing process, it can have a grinding efficiency for 400 percent greater than that of natural diamond. For example, to remove a zirconia crown from a patient's mount, it would take more than one electroplated diamond dental burr. However, a vacuum brazed diamond dental burr made for synthetic diamond can remove at least 4 crowns.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a side view of a typical dental burr in accordance with the present invention;

FIG. 2 is a detailed view of the dental burr of FIG. 2 partially broken away;

FIG. 3 is a sectional view of a "green" structure prior to brazing of the dental burrs of the present invention;

FIG. 4 is a detailed sectional view showing the brazed structure of the dental burrs of the present invention.

FIG. 5 is a perspective view showing dental burrs in a graphite tray;

FIG. 6 is a perspective view showing another shape of a dental burr;

FIG. 7 is a perspective view showing another shape of a dental burr.

DETAILED DESCRIPTION OF THE PREFERRED EMBODIMENTS

The following description of the preferred embodiments is merely exemplary in nature and is in no way intended to limit the invention, its application, or uses.

In accordance with the present invention, there is provided a dental burr 10, 10a, 10b which is unique in that it uses a synthetic diamond grit material 12 brazedly attached to a work surface 14 of the dental burr 10. The dental burr tool 10 includes a shaft portion 16 and a working portion 18 which contains on its outer surface 14 a synthetic diamond abrasive grit cutting surface. The synthetic diamond 12 is brazedly attached to the surface.

Synthetic diamond 12 used in the present invention is preferably the stronger, purer, less friable, blockier grades, such as a Diamond Innovations MBG 660 Ti (Ti coated synthetic diamond, made by the old GE Factory, now owned by Sandik).

Generally, the grit size ranges of the dental 60/80 to 325/400 typically80/100 to 230/270 and preferably 100/120 to 200/230. Synthetic diamond 12 is distinguished from natural diamond particles in the following manner. Synthetic diamond, 12 if untreated, exhibits ferromagnetism. Therefore, because all burrs were electroplate synthetice diamond cannot be used as it will interfere with the electorplating process. Thus, it is not possible to electroplate with synthetic diamond, unless is has been specially treated at high temperatures to eliminate its conductive properties and that high temperature process substantially weakens the diamond. So, the cost of the diamond is higher because of the additional processing to treat synthetic diamond to make it useable in electroplating would result in nothing better than natural diamond. However, we have discovered that brazing unprocessed synthetic diamond can be accomplished without loss of its superior properties.

Uncoated synthetic diamond or synthetic diamond coated with a carbide forming substance may be used in the present invention. The process for brazing is set forth in my co-pending application and patents as referenced below. Generally, A typical carbide forming substance 24, such as molybdenum powder, is preferably coated on the synthetic diamond before brazing or may also be mixed in with the braze 14. Other carbide forming materials such as SI, Mo, CR, Ti, Fe, TiH or mixtures thereof may be used. Typically a binder is used to bind the diamonds and the braze material to the substrate. A number of these burrs is then placed in a graphite tray 26. And the tray is placed in an oven for brazing. As an example an Induction heated vacuum furnace such as a GH Group Model VF-40 furnace is suitable for use The synthetic diamond is brazed at a temperature of generally 875 C to 1100 C typically 890 C to 1000 C and preferably 910 C to 990 C. The diamond does not develop the carbide coating if too cool, if too hot the synthetic diamond can degrade and the braze can decompose and metal becomes weaker. Therefor precision heating as described in my copending application allows precision heating of the synthetic diamond.

The induction furnace is held in a range of vacuum of: $4 \times 10-3$ torr to $5 \times 10-8$ torr or $5 \times 10-4$ torr to $4 \times 10-8$ torr or $4 \times 10-5$ torr to $4 \times 10-7$ torr.

Further information regarding the present invention including the process of manufacture of my copending application entitled "INDUCTION HEATED VACUUM FURNACE FOR MAKING BRAZED DIAMOND DENTAL BURRS" which was filed on the same date as the present application; as well as my U.S. Pat. Nos. 4,968,326 and 4,776,862, all of which are incorporated herein by reference thereto.

A process of removing a high hardness dental material is also provided using a dental burr made in accordance with this invention. The dental burr of the present invention allows the dentist to grind out high hardness fillings in one two three or multiple teeth using a single burr whereas a prior art electroplated dental burr would not last as long perhaps not even long enough for the material in one tooth.

The process includes providing a tooth which includes a high hardness dental material to be removed from a patient. A dental burr made in accordance with the teachings of the present invention is also provided. The dental burr has a working surface including a synthetic diamond grit material brazedly attached to a dental burr. A dental tool which receives said dental burr of step b. which is adapted for grinding of the high hardness dental material. The tool and brazed synthetic diamond grit bur is use to grind the high hardness material from the tooth with said synthetic diamond abrasive brazed dental burr.

Advantageously the process of the present invention works with high hardness and wear resistant modern dentistry materials. Use of synthetic diamond grit braze bonded to a dental burr provides much stronger bonds of the grit particles and a superior dental burr for use in grinding modern high hardness and wear resistant dental materials. It can be used by a dentist in procedures involving more than one, two and/or three teeth far exceeding capabilities in electroplated natural diamond dental burrs in use today.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A dental burr comprising:
a dental burr tool substrate including a shaft portion and a working portion which contains on its outer surface synthetic diamond abrasive grit which is a strong, pure, blocky grade synthetic diamond and the synthetic diamond is unprocessed for removal of ferromagnetic properties and the synthetic diamond is less friable than natural diamond, and a carbide forming brazing alloy to form a cutting surface, wherein the synthetic diamond is brazedly attached to the surface.

2. The dental burr of claim 1 further comprising a synthetic diamond particle size of from about 60/80 grit to about 325/400 grit.

3. The dental burr of claim 1 wherein the synthetic diamond material is uncoated.

4. The dental burr of claim 1 wherein the synthetic diamond has a carbide forming substance coating the synthetic diamond.

5. The dental burr of claim 4 wherein the carbide forming substance is selected from the group comprising SI, Mo, CR, Ti, Fe, TiH or mixtures thereof.

6. A process for manufacture of a dental burr comprising:
providing a plurality of dental burr tools each including a shaft portion and a cutting head portion;
coating the cutting head portion with a mixture of a carbide forming braze and synthetic diamond abrasive grit which is blocky grade synthetic diamond and the synthetic diamond is unprocessed for removal of ferromagnetic properties and which is less friable than natural diamond;
placing the plurality of dental burr tools on a graphite tray;
induction heating the plurality of dental burr tools in an induction oven with a graphite induction heated hot zone for precision heating said plurality of dental burrs at a temperature for brazing of the diamond to the cutting head, wherein the temperature is 890° C. to 1000° C.

7. The process for manufacture of a dental burr of claim 6 further comprising coating the synthetic diamond with a carbide forming material.

8. A process of removing a high hardness dental material comprising:
a. providing a tooth which includes a high hardness dental material to be removed from a patient;
b. providing a dental burr having a working surface including synthetic diamond grit material which is blocky grade synthetic diamond and the synthetic diamond is unprocessed for removal of ferromagnetic properties and which is less friable than natural diamond, and a carbide forming brazing alloy brazedly attached to said dental burr in an induction furnace held in a range of vacuum of about $4 \times 10^{-3}$ torr;
c. providing a dental tool which receives said dental burr of step b. which is adapted for grinding of the tooth and,
d. grinding the high hardness material from the tooth with said synthetic diamond abrasive brazed dental burr.

9. The process of claim 8 wherein said high hardness material is a Zirconia or Maicor dental material.

10. The process of claim 9, wherein said tool is a rotary tool.

11. The process of claim 8 wherein the process is used with more than one tooth with the same dental burr.

12. The process of claim 8 wherein the process is used with more than two teeth with the same dental burr.

13. The process of claim 8 wherein the process is used with more than three teeth with the same dental burr.

14. The dental burr of claim 1, wherein said synthetic diamond abrasive grit is MBG 660.

15. The dental burr of claim 6, wherein said synthetic diamond abrasive grit is MBG 660.

16. The dental burr of claim 8, wherein said synthetic diamond abrasive grit is MBG 660.

* * * * *

UNITED STATES PATENT AND TRADEMARK OFFICE
CERTIFICATE OF CORRECTION

PATENT NO. : 10,064,702 B2
APPLICATION NO. : 14/689545
DATED : September 4, 2018
INVENTOR(S) : Ronald C. Wiand Page 1 of 1

It is certified that error appears in the above-identified patent and that said Letters Patent is hereby corrected as shown below:

In the Specification

Column 2,
Line 12, "FIG. 2 is a detailed view of the dental burr of FIG. 2" should be -- FIG. 2 is a detailed view of the dental burr of FIG. 1 --

Column 2,
Line 49, "synthetice" should be -- synthetic --

Column 2,
Line 50, "electorplating" should be -- electroplating --

Column 3,
Lines 16-18, "The induction furnace is held in a range of vacuum of: 4 × 10-3 torr to 5 × 10-8 torr or 5 × 10-4 torr to 4 × 10-8 torr or 4 × 10-5 torr to 4 × 10-7 torr." should be -- The induction furnace is held in a range of vacuum of: $4 \times 10^{-3}$ torr to $5 \times 10^{-8}$ torr or $5 \times 10^{-4}$ torr to $4 \times 10^{-8}$ torr or $4 \times 10^{-5}$ torr to $4 \times 10^{-7}$ torr. --

Column 3,
Line 42, "bur" should be -- burr --

Signed and Sealed this
Fourth Day of December, 2018

Andrei Iancu
*Director of the United States Patent and Trademark Office*